(12) United States Patent
Josch et al.

(10) Patent No.: US 10,421,700 B2
(45) Date of Patent: *Sep. 24, 2019

(54) PROCESS FOR PREPARING 1,3-BUTADIENE FROM N-BUTENES BY OXIDATIVE DEHYDROGENATION

(71) Applicants: BASF SE, Ludwigshafen (DE); Linde AG, Munich (DE)

(72) Inventors: Jan Pablo Josch, Neustadt (DE); Ragavendra Prasad Balegedde Ramachandran, Limburgerhof (DE); Christian Walsdorff, Ludwigshafen (DE); Regina Benfer, Altrip (DE); Anton Wellenhofer, Hohenschaeftlarn (DE); Ulrike Wenning, Pullach (DE); Heinz Boelt, Wolfratshausen (DE); Hendrik Reyneke, Munich (DE); Christine Toegel, Neubiberg (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/561,711

(22) PCT Filed: Mar. 23, 2016

(86) PCT No.: PCT/EP2016/056363
§ 371 (c)(1),
(2) Date: Sep. 26, 2017

(87) PCT Pub. No.: WO2016/151008
PCT Pub. Date: Sep. 29, 2016

(65) Prior Publication Data
US 2018/0105479 A1    Apr. 19, 2018

(30) Foreign Application Priority Data

Mar. 26, 2015 (EP) .................................. 15161096

(51) Int. Cl.
*C07C 5/48* (2006.01)
*C07C 7/00* (2006.01)
(Continued)

(52) U.S. Cl.
CPC ................ *C07C 5/48* (2013.01); *C07C 7/005* (2013.01); *C07C 7/08* (2013.01); *C07C 7/09* (2013.01); *C07C 7/11* (2013.01); *C07C 11/167* (2013.01)

(58) Field of Classification Search
CPC .. C07C 5/48; C07C 7/08; C07C 7/005; C07C 7/11; C07C 11/167
See application file for complete search history.

(56) References Cited

U.S. PATENT DOCUMENTS 3,110,746 A    11/1963   Voge et al.
3,232,027 A     2/1966   Lorenz et al.
(Continued)

FOREIGN PATENT DOCUMENTS

DE    2440329 A1    3/1975
DE    2530959 A1    2/1976
(Continued)

OTHER PUBLICATIONS

U.S. Appl. No. 15/514,077, filed Mar. 24, 2017.
(Continued)

*Primary Examiner* — In Suk C Bullock
*Assistant Examiner* — Ali Z Fadhel
(74) *Attorney, Agent, or Firm* — Drinker Biddle & Reath LLP

(57) ABSTRACT

The invention relates to a process for producing butadiene from n-butenes which comprises the steps of:
A) providing a vaporous n-butenes-comprising input gas stream a1 by evaporating a liquid n-butenes-comprising stream a0;

(Continued)

B) introducing the vaporous n-butenes-comprising input gas stream a1 and an at least oxygenous gas into at least one oxidative dehydrogenation zone and oxidatively dehydrogenating n-butenes to butadiene to obtain a product gas stream b comprising butadiene, unconverted n-butenes, steam, oxygen, low-boiling hydrocarbons, high-boiling secondary components, possibly carbon oxides and possibly inert gases, Ca) chilling the product gas stream b by contacting with a cooling medium comprising an organic solvent in at least one chilling zone, the cooling medium being at least partially recycled into the chilling zone, Cb) compressing the chilled product gas stream b which is possibly depleted of high-boiling secondary components in at least one compression stage to obtain at least one aqueous condensate stream c1 and a gas stream c2 comprising butadiene, n-butenes, steam, oxygen, low-boiling hydrocarbons, possibly carbon oxides and possibly inert gases, D) removing noncondensable and low-boiling gas constituents comprising oxygen, low-boiling hydrocarbons, possibly carbon oxides and possibly inert gases as gas stream d2 from the gas stream c2 by absorbing the $C_4$ hydrocarbons comprising butadiene and n-butenes into an absorption medium to obtain a $C_4$-hydrocarbons-laden absorption medium stream and the gas stream d2 and subsequently desorbing the $C_4$ hydrocarbons from the laden absorption medium stream to obtain a $C_4$ product gas stream d1, wherein at least some of the recycled cooling medium from step Ca) is brought into thermal contact with the liquid n-butenes-comprising stream a0 in one or more indirect heat exchangers and at least some of the liquid n-butenes-comprising stream a0 is evaporated by indirect heat transfer with the recycled cooling medium.

13 Claims, 4 Drawing Sheets

(51) Int. Cl.
  C07C 7/08   (2006.01)
  C07C 7/09   (2006.01)
  C07C 7/11   (2006.01)
  C07C 11/167 (2006.01)

(56) References Cited

U.S. PATENT DOCUMENTS

| | | | |
|---|---|---|---|
| 3,890,123 A | 6/1975 | Kuga | |
| 3,911,039 A | 10/1975 | Grasselli et al. | |
| 4,162,234 A | 7/1979 | Grasselli et al. | |
| 4,174,354 A | 11/1979 | Grasselli et al. | |
| 4,336,409 A | 6/1982 | Yamamoto et al. | |
| 4,397,771 A | 8/1983 | Grasselli et al. | |
| 4,423,281 A | 12/1983 | Yamamoto et al. | |
| 4,424,141 A | 1/1984 | Grasselli et al. | |
| 4,547,615 A | 10/1985 | Yamamoto | |
| 4,595,788 A * | 6/1986 | Yamamoto | C07C 5/48 585/621 |
| 9,957,208 B2 * | 5/2018 | Grune | C07C 7/09 |
| 2012/0130137 A1 | 5/2012 | Orita et al. | |
| 2014/0100399 A1 * | 4/2014 | Brummer | C07C 7/10 585/259 |
| 2014/0114108 A1 * | 4/2014 | Yano | C07C 5/48 585/506 |
| 2014/0200381 A1 * | 7/2014 | Josch | C07C 7/05 585/621 |
| 2015/0073184 A1 * | 3/2015 | Caciula | C07C 5/09 585/254 |
| 2015/0126788 A1 * | 5/2015 | Takagaki | C07C 7/10 585/326 |
| 2016/0122264 A1 | 5/2016 | Olbert et al. | |
| 2016/0152531 A1 | 6/2016 | Walsdorff et al. | |
| 2016/0347686 A1 | 12/2016 | Grune et al. | |
| 2016/0355450 A1 | 12/2016 | Grune et al. | |
| 2017/0008867 A1 | 1/2017 | Galeano Nunez et al. | |
| 2017/0233313 A1 | 8/2017 | Grune et al. | |
| 2017/0334809 A1 | 11/2017 | Grune et al. | |

FOREIGN PATENT DOCUMENTS

| | | | |
|---|---|---|---|
| DE | 2600128 A1 | 7/1976 | |
| JP | 2010090083 A | 4/2010 | |
| JP | 2011001341 A | 1/2011 | |
| JP | 2011006381 A | 1/2011 | |
| JP | 2012072086 A | 4/2012 | |
| JP | 2012240963 A | 12/2012 | |
| JP | 2013119530 A | 6/2013 | |
| JP | 2013177380 A | 9/2013 | |
| KR | 20130036467 A * | 10/2011 | B01J 23/31 |
| KR | 20130036467 A | 4/2013 | |
| KR | 20130036468 A | 4/2013 | |
| WO | WO-2013148908 A1 | 10/2013 | |
| WO | WO-2014111409 A1 | 7/2014 | |
| WO | WO-2015007698 A1 | 1/2015 | |
| WO | WO-2015055613 A1 | 4/2015 | |

OTHER PUBLICATIONS

U.S. Appl. No. 15/525,330, filed May 9, 2017.
English Translation of International Preliminary Report on Patentability for International ApplicationNo. PCT/EP2016/056363.
Jung, J. C., et al., "Catalytic performace of bismuth molybdate catalysts in the oxidative dehydrogenation of C4 raffinate-3 to 1,3 butadiene", Applied Catalysis A: General, 2007, vol. 317, pp. 244-249.
Jung, J.C., et al., "Production of 1,3-Butadiene From C4 Raffinate-3 Through Oxidative Dehydrogenation of n--Butene Over Bismuth Molybdate Catalysts", Catal. Surv. Asia, 2009, vol. 13, pp. 78-93.
International Preliminary Report on Patentabiliy for PCT/EP2016/055408 dated Feb. 22, 2017 (in German).
International Preliminary Report on Patentabiliy for PCT/EP2016/056363 dated Mar. 8, 2017 (in German).
International Search Report for PCT/EP2016/055408 dated May 11, 2016.
International Search Report for PCT/EP2016/056363 dated Jun. 1, 2016.
Written Opinion of the International Searching Authority for PCT/EP2016/055408 dated May 11, 2016 (in Germany).
Written Opinion of the International Searching Authority for PCT/EP2016/056363 dated Jun. 1, 2016.

* cited by examiner

PROCESS FOR PREPARING 1,3-BUTADIENE FROM N-BUTENES BY OXIDATIVE DEHYDROGENATION

CROSS-REFERENCE TO RELATED APPLICATIONS

This application is a national stage application (under 35 U.S.C. § 371) of PCT/EP2016/056363, filed Mar. 23, 2016, which claims benefit of European Application No. 15161096.1, filed Mar. 26, 2015, both of which are incorporated herein by reference in their entirety.

The invention relates to a process for producing 1,3-butadiene (butadiene) from n-butenes by oxidative dehydrogenation (ODH).

Butadiene is an important commodity chemical and is used, for example, for producing synthetic rubbers (butadiene homopolymers, styrene-butadiene rubber or nitrile rubber) or for producing thermoplastic terpolymers (acrylonitrile-butadiene-styrene copolymers). Butadiene is also converted to sulfolane, chloroprene and 1,4-hexamethylenediamine (via 1,4-dichlorobutene and adiponitrile). Via dimerization of butadiene, it is further possible to prepare vinylcyclohexene, which may be dehydrogenated to styrene.

Butadiene may be produced by thermal cracking (steam cracking) of saturated hydrocarbons, typically proceeding from naphtha as feedstock. Steam cracking of naphtha generates a hydrocarbon mixture of methane, ethane, ethene, acetylene, propane, propene, propyne, allene, butanes, butenes, 1,3-butadiene and 1,2-butadiene, butynes, methylallene, and $C_5$ and higher hydrocarbons.

Butadiene may also be obtained by oxidative dehydrogenation of n-butenes (1-butene and/or 2-butene). The input gas used for oxidative dehydrogenation (oxydehydrogenation, ODH) of n-butenes to butadiene may be any desired mixture comprising n-butenes. For example, it is possible to use a fraction which comprises n-butenes (1-butene and/or 2-butene) as the main constituent and has been obtained from the $C_4$ fraction from a naphtha cracker by removing butadiene and isobutene. Also useable as input gas are gas mixtures which comprise 1-butene, cis-2-butene, trans-2-butene or mixtures thereof and have been obtained by dimerization of ethylene. Further mixtures usable as input gas are n-butenes-comprising gas mixtures obtained by fluid catalytic cracking (FCC).

Oxidative dehydrogenation of n-butenes to butadiene is performed at temperatures of, for example, 400° C. in the gas phase.

Processes for oxidative dehydrogenation of butenes to butadiene are known in principle.

US 2012/0130137 A1, for example, describes a process of this kind using catalysts comprising oxides of molybdenum, bismuth and generally further metals. In order for such catalysts for oxidative dehydrogenation to show lasting activity, a critical minimum partial oxygen pressure in the gas atmosphere is required to avoid excessive reduction and hence loss of performance of the catalysts. It is thus generally also not possible to operate with a stoichiometric oxygen input or with complete oxygen conversion in the oxydehydrogenation reactor (ODH reactor). US 2012/0130137 describes, for example, an oxygen content of from 2.5 to 8 vol % in the starting gas.

The need for an oxygen excess for such catalyst systems is common knowledge and is reflected in the process conditions when such catalysts are used. Cited here as representative examples are the more recent publications of Jung et al. (Catal. Surv. Asia 2009, 13, 78-93; DOI 10.1007/s10563-009-9069-5 and Applied Catalysis A: General 2007, 317, 244-249; DOI 10.1016/j.apcata.2006.10.021).

Catalytic oxidative dehydrogenation can form high-boiling secondary components, for example maleic anhydride, phthalic anhydride, benzaldehyde, benzoic acid, ethylbenzene, styrene, fluorenone, anthraquinone and others. Deposits of these components can result in blockages and an increased pressure drop in the reactor or downstream of the reactor in the work-up region and can thus disrupt controlled operation. Deposits of the cited high-boiling secondary components can also impair the function of heat exchangers or damage apparatuses with moving parts such as compressors. Steam-volatile compounds such as fluorenone may advance through a water-operated quench apparatus and precipitate downstream thereof in the gas discharge lines. There is thus also a general danger of solid deposits getting into downstream apparatus parts, for example compressors, and causing damage thereto.

US 2012/0130137 A1 also makes reference to the problem of high-boiling by-products. Particular mention is made of phthalic anhydride, anthraquinone and fluorenone, it being reported that said by-products are typically present in the product gas in concentrations of from 0.001 to 0.10 vol %. US 2012/0130137 A1 recommends cooling down the hot reactor output gases directly by contact with a cooling liquid (quench tower), typically to an initial temperature of from 5° C. to 100° C. Cited cooling liquids are water and aqueous alkali solutions.

JP-A 2011-001341 describes two-stage cooling for a process for oxidative dehydrogenation of alkenes to conjugated alkadienes. This comprises initially chilling the product output gas from the oxidative dehydrogenation to a temperature between 300° C. and 221° C. and then further chilling said gas to a temperature between 99° C. and 21° C.

JP-A 2013-119530 describes a quench in which an ODH product gas is cooled by direct contact with water.

JP-A 2013-177380 describes possible coolants used in the product gas quench. Generally cited as cooling liquid are saturated hydrocarbons, unsaturated hydrocarbons, aromatic hydrocarbons, esters, ethers, aldehydes, ketones, amines, acids, water and mixtures thereof. Water is preferred as coolant.

KR 2013-0036467 and KR 2013-0036468 describe the use of a mixture of water and a water-miscible organic solvent as coolant in a product gas quench of an oxydehydrogenation. Due to its water miscibility, work-up and regeneration of the organic solvent is highly energy intensive and economically disadvantageous.

The input stream comprising n-butenes is typically in liquid form. Said stream is typically provided via a pipeline from other production sites within a larger integrated petrochemical site or is stocked in large storage tanks. In pressure tanks $C_4$ hydrocarbons are typically stored at room temperature.

At a typical process pressure of about 6 to 7 bar the evaporation temperature of n-butenes is about 60° C. Heat for evaporating the n-butenes-comprising input stream must therefore be provided by a heat-transfer medium having a temperature of >60° C. Since the specific heat of vaporization of the n-butenes is relatively high and operating an ODH plant necessitates evaporation of large mass flows, the heat requirements for evaporating liquid n-butenes are very high. Liquid n-butenes-comprising input streams are generally heated up and evaporated using low-pressure steam. Said steam is generally available at a pressure of from about 2 to about 5 bar and has a condensation temperature of from about 120° C. to about 150° C.

However, low-pressure steam is relatively expensive. There is also the problem that the process pressure in the evaporator may be higher on the n-butenes side than on the low-pressure steam side which has the effect that in case of leaks at the joints between the tube plate and the tubes of the evaporator for example, $C_4$ hydrocarbons can get into the steam condensate. However, contaminated steam condensate needs to be processed before further use which can incur additional costs. Furthermore, the large temperature difference between the steam condensate on the one hand (for example 150° C.) and the evaporating n-butenes-comprising stream on the other hand (about 60° C.) can result in unstable operating conditions in the evaporator, for example highly variable unstable heat transfer in the transition between nucleate boiling and film boiling.

It is an object of the present invention to provide a process which remedies the abovementioned disadvantages of known processes. It is a particular object of the present invention to provide an economic process where the evaporation of the liquid, n-butenes-comprising input stream does not incur great additional costs and where unstable operating conditions during the evaporation are avoided.

The object is achieved by a process for producing butadiene from n-butenes, comprising the steps of:

A) providing a vaporous n-butenes-comprising input gas stream a1 by evaporating a liquid n-butenes-comprising stream a0;

B) introducing the vaporous n-butenes-comprising input gas stream a1 and an oxygenous gas into at least one oxidative dehydrogenation zone and oxidatively dehydrogenating n-butenes to butadiene to obtain a product gas stream b comprising butadiene, unconverted n-butenes, steam, oxygen, low-boiling hydrocarbons, high-boiling secondary components, possibly carbon oxides and possibly inert gases, Ca) chilling the product gas stream b by contacting with a cooling medium comprising an organic solvent in at least one chilling zone, the cooling medium being at least partially recycled into the chilling zone, Cb) compressing the chilled product gas stream b which is possibly depleted of high-boiling secondary components in at least one compression stage to obtain at least one aqueous condensate stream c1 and a gas stream c2 comprising butadiene, n-butenes, steam, oxygen, low-boiling hydrocarbons, possibly carbon oxides and possibly inert gases, D) removing noncondensable and low-boiling gas constituents comprising oxygen, low-boiling hydrocarbons, possibly carbon oxides and possibly inert gases as gas stream d2 from the gas stream c2 by absorbing the $C_4$ hydrocarbons comprising butadiene and n-butenes into an absorption medium to obtain a $C_4$-hydrocarbons-laden absorption medium stream and the gas stream d2 and subsequently desorbing the $C_4$ hydrocarbons from the laden absorption medium stream to obtain a $C_4$ product gas stream d1, wherein at least some of the recycled cooling medium from step Ca) is brought into thermal contact with the liquid n-butenes-comprising stream a0 in one or more indirect heat exchangers and at least some of the liquid n-butenes-comprising stream a0 is evaporated by indirect heat transfer with the recycled cooling medium.

Figure 1:
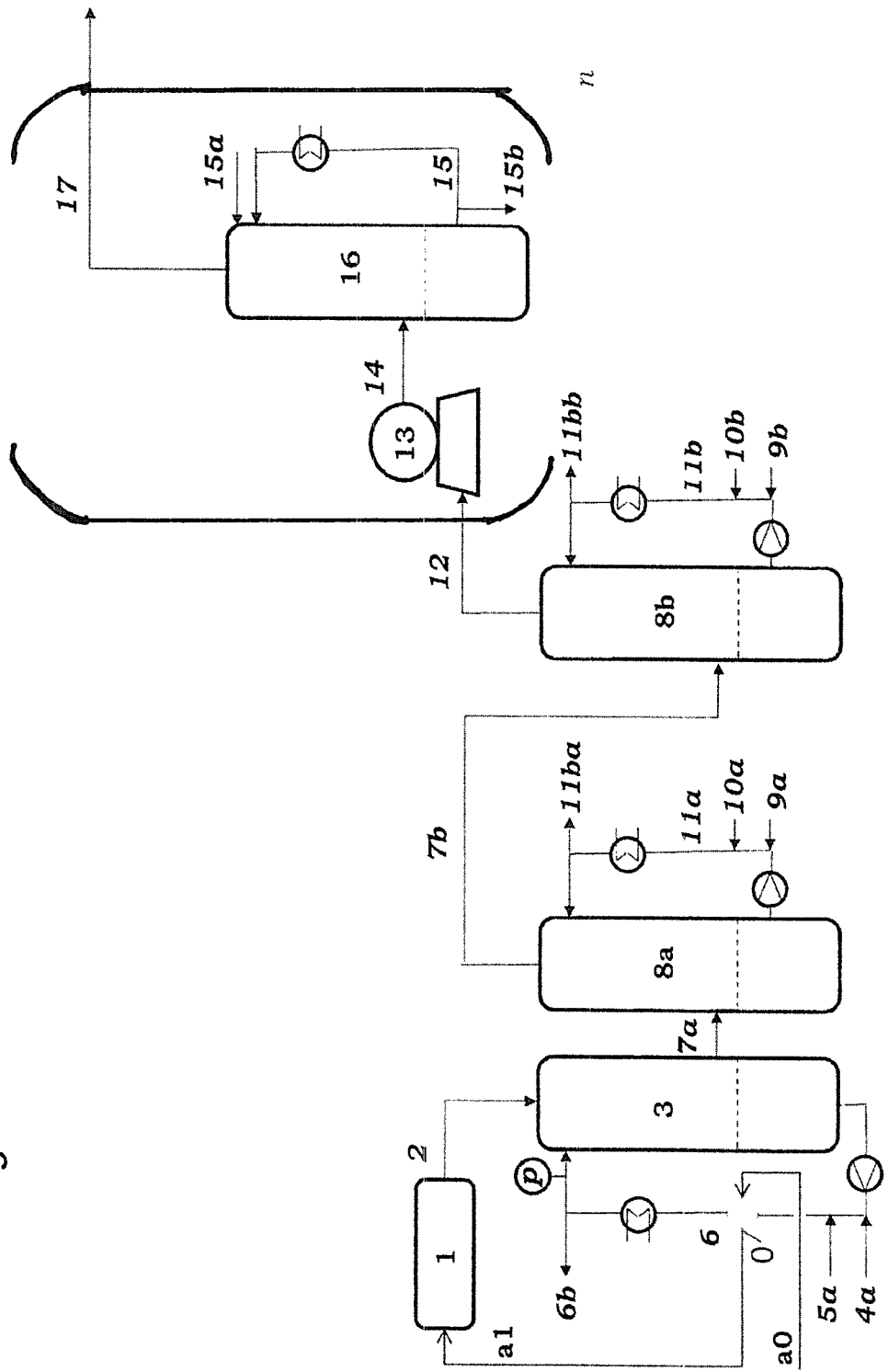
FIG. 1 shows an embodiment in which the biphasic coiling medium is brought into thermal contact with the liquid n-butenes -comprising input stream a0 in the heat exchanger 0.

The process according to the invention makes it possible to reduce the amount of low-pressure steam required for the evaporation of the liquid, n-butenes-comprising stream a0. Low-pressure steam is preferably completely eschewed. There is thus also no danger of the low-pressure steam condensate being contaminated with the organic components to be evaporated (n-butenes and other hydrocarbons) as a result of leaks. The process according to the invention at least reduces the amount of potentially contaminated low-pressure steam condensate.

The small temperature difference between the temperature of the recycled cooling medium and the evaporation temperature of the n-butenes-comprising stream a0 to be evaporated also solves the problem of variable unstable heat transfer in the transition between nucleate boiling and film boiling because small temperature differences naturally result in operation outside the transition between nucleate boiling and film boiling.

During heat transfer the temperature difference between the recycled cooling medium and the stream a0 to be evaporated is generally from 2° C. to 40° C., preferably from 2° C. to 30° C.

The temperature of the recycled cooling medium during heat transfer is generally in the range of from 80° C. to 60° C., preferably in the range of from 66° C. to 60° C.

In general, the evaporation temperature of the liquid n-butenes-comprising stream a0 is in the range of from 30° C. to 70° C., preferably of from 35° C. to 65° C. The liquid n-butenes-comprising stream a0 is at a pressure of generally from 4 to 8 bar, preferably from 5 to 7 bar.

The indirect heat exchanger(s) in which at least some of the recycled cooling medium is brought into thermal contact with the liquid n-butenes-comprising stream a0 are preferably straight-tube heat exchangers with a floating head and a vapor separation space (for example TEMA BES type).

In addition, further heat exchangers may be operated with low-pressure steam, i.e. some of the total heat energy required for evaporating the n-butenes-comprising input gas stream a0 may still be provided by low-pressure steam.

It is preferable when the cooling medium employed in step Ca) comprises as organic solvent one or more aromatic hydrocarbons, particular preference being given to toluene, o-xylene, m-xylene, p-xylene, mesitylene, mono-, di- and triethylbenzene, mono-, di- and triisopropylbenzene and mixtures thereof.

The cooling medium may comprise an aqueous phase and an organic phase.

When the cooling medium comprises an aqueous phase and an organic phase, it is preferable for at least some of the aqueous phase to be removed from the aqueous phase by phase separation and the removed aqueous phase to be brought into thermal contact with the liquid n-butenes-comprising stream a0. It is likewise possible for at least some of the organic phase to be removed and the removed organic phase to be brought into thermal contact with the liquid n-butenes-comprising stream a0.

In one embodiment of the invention the cooling medium comprises an aqueous phase and an organic phase. Continuous operation of the quench circuit can be possible for longer when the circuit is operated with two mutually immiscible coolants. Continuous operation is further possible for a particularly long period when the two immiscible solvents are present in a particular ratio on entry into the quench column. Continuous operation is further possible for a particularly long period when the two immiscible solvents are intimately dispersed with one another on entry into the quench column.

In this embodiment the chilling stage Ca) employs a biphasic dispersion of one or more solvents and an aqueous phase. The rapid chilling of the product gas stream in the quench results in condensation of high-boiling secondary components. Organic solvents generally have a very much higher dissolution capacity for the high-boiling by-products that can lead to deposits and blockages in the plant parts downstream of the ODH reactor than do water or aqueous alkaline solutions. Preferably employed organic solvents are aromatic hydrocarbons, particular preference being given to toluene, o-xylene, m-xylene, p-xylene, mesitylene, mono-, di- and triethylbenzene, mono-, di- and triisopropylbenzene and mixtures thereof.

The presence of an additional aqueous phase in the circulating cooling medium can achieve effective avoidance of blockages in the quench circuit, especially in the region of the nozzles through which the coolant enters the quench column, but also, for example, in the pumps of the coolant circuit and in analytical instruments which measure the volume flow rate of the circuit. This is attributed to the fact that the condensed high-boiling secondary components also include substances which have only a low solubility in an organic solvent but have substantially better solubility in water or aqueous solutions. This leads to tackifying substances being dissolved in the organic and aqueous phase which has the effect that coke-like insoluble solids remain dispersed in the coolant circuit, and are not deposited on plant parts such as nozzles and do not lead to blockages there.

The phase ratio, i.e. the ratio of the mass of the aqueous phase to the mass of the organic phase of the cooling medium on entry into the chilling stage (quench stage) before contacting, is determined via the flow rates of the aqueous and organic coolants added to the coolant circuit, the flow rate of steam present in the product gas stream, the flow rates of steam and organic coolant which exit the chilling stage, and the flow rates of the aqueous and organic phases which are withdrawn from the coolant circuit as output stream (purge). The phase ratio is preferably not less than 0.15:1, more preferably not less than 0.18:1 and in particular not less than 0.2:1 and not more than 100:1, preferably not more than 10:1, more preferably not more than 2:1, in particular not more than 1:1.

It is preferable when the cooling medium exhibits very thorough dispersion of both phases on entry into the chilling zone. A high degree of dispersion of the cooling medium may be effected by installing suitable mixers into the circuit, for example. The type of mixer is not subject to particular restriction here and comprises stirrers, static mixers and orifice mixers.

The cooling medium is generally introduced into the chilling zone(s) through one or more nozzles. In one preferred embodiment, a flow having a Reynolds number Re of at least 1000 is generated in this or these nozzle(s). The power input here is at least $10^3$ W/m$^3$. In particular, this achieves such thorough dispersion of the two phases that the coefficient of variation for each component of each phase of the cooling medium on entry into the chilling zones is less than 1.

Embodiments which follow are preferred or particularly preferred versions of the process according to the invention:

Stage Ca) is performed in a plurality of stages Ca1) to Can), preferably in two stages Ca1) and Ca2). Here, at least some of the cooling medium may be supplied as chillant to the first stage Ca1) after it has passed through the second stage Ca2).

Stage Cb) generally comprises at least one compression stage Cba) and at least one chilling stage Cbb). It is preferable when in the at least one chilling stage Cbb) the gas compressed in the compression stage Cba) is contacted with a chillant. It is particularly preferable when the chillant of the chilling stage Cbb) comprises the same organic solvent used as chillant in stage Ca). In one particularly preferred version, at least some of this chillant is supplied as chillant to stage Ca) after it has passed through the at least one chilling stage Cbb).

It is preferable when stage Cb) comprises a plurality of compression stages Cba1) to Cban) and chilling stages Cbb1) to Cbbn), for example four compression stages Cba1) to Cba4) and four chilling stages Cbb1) to Cbb4).

Step D) preferably comprises steps Da) to Dc):

Da) absorbing the $C_4$ hydrocarbons comprising butadiene and n-butenes into a high-boiling absorption medium to obtain a $C_4$-hydrocarbons-laden absorption medium stream and the gas stream d2, Db) removing oxygen from the $C_4$-hydrocarbons-laden absorption medium stream from step Da) by stripping with a noncondensable gas stream, and Dc) desorbing the $C_4$ hydrocarbons from the laden absorption medium stream to obtain a $C_4$ product gas stream d1 consisting essentially of $C_4$ hydrocarbons and comprising less than 100 ppm of oxygen.

The high-boiling absorption medium employed in step Da) is preferably an aromatic hydrocarbon solvent, more preferably the aromatic hydrocarbon solvent employed in step Ca), in particular toluene, o-xylene, m-xylene, p-xylene, mesitylene or mixtures thereof.

It is preferable when step D) is followed by further steps E) and F):

E) separating the $C_4$ product stream d1 into a stream e1 comprising butadiene and the selective solvent and a stream e2 comprising n-butenes by extractive distillation with a butadiene-selective solvent, F) distilling the stream e1 comprising butadiene and the selective solvent to obtain a stream f1 consisting essentially of the selective solvent and a stream f2 comprising butadiene.

A step A) comprises providing an n-butenes-comprising input gas stream.

Usable as input gas stream are pure n-butenes (1-butene and/or cis-/trans-2-butene) but also gas mixtures comprising butenes. Such a gas mixture may be obtained, for example, by nonoxidative dehydrogenation of n-butane. It is also possible to use a fraction which comprises n-butenes (1-butene and cis/trans-2-butene) as the main constituent and has been obtained from the $C_4$ fraction from naphtha cracking by removal of butadiene and isobutene. Also useable as input gas are gas mixtures which comprise pure 1-butene, cis-2-butene, trans-2-butene or mixtures thereof and which have been obtained by dimerization of ethylene. Further mixtures usable as the input gas are n-butenes-comprising gas mixtures obtained by fluid catalytic cracking (FCC).

The liquid n-butenes-comprising stream generally comprises from 50 to 100 wt % of n-butenes (1-butene, cis-/trans-2-butene), from 0 to 10 wt % of isobutene, from 0 to 50 wt % of n-butane, from 0 to 20 wt % of isobutane, from 0 to 10 wt % of $C_1$, $C_2$ and $C_3$ hydrocarbons and from 0 to 10 wt % of $C_5^+$ hydrocarbons.

The stream a0 is generally at a pressure of from 4 to 8 bar, preferably from 5 to 7 bar. The evaporation temperature of said stream is generally from 30° C. to 70° C., preferably from 35° C. to 65° C.

Step B) comprises introducing the n-butenes-comprising input gas stream and at least one oxygenous gas into at least one dehydrogenation zone and oxidatively dehydrogenating the butenes present in the gas mixture to butadiene in the presence of an oxydehydrogenation catalyst.

Catalysts suitable for the oxydehydrogenation are generally based on an Mo—Bi—O-containing multimetal oxide system which generally further comprises iron. The catalyst system generally further comprises additional components, for example potassium, cesium, magnesium, zirconium, chromium, nickel, cobalt, cadmium, tin, lead, germanium, lanthanum, manganese, tungsten, phosphorus, cerium, aluminum or silicon. Iron-containing ferrites too have been proposed as catalysts.

In one preferred embodiment the multimetal oxide comprises cobalt and/or nickel. In a further preferred embodiment the multimetal oxide comprises chromium. In a further preferred embodiment the multimetal oxide comprises manganese.

Examples of Mo—Bi—Fe—O-containing multimetal oxides include Mo—Bi—Fe—Cr—O— or Mo—Bi—Fe—Zr—O-containing multimetal oxides. Preferred systems are described, for example, in U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$), U.S. Pat. No. 4,424,141 ($Mo_{12}BiFe_3Co_{4.5}Ni_{2.5}P_{0.5}K_{0.1}O_x+SiO_2$), DE-A 25 30 959 ($Mo_{12}BiFe_3Co_{4.5}Ni_{2.5}Cr_{0.5}K_{0.1}O_x$, $Mo_{13.75}BiFe_3Co_{4.5}Ni_{2.5}Ge_{0.5}K_{0.8}O_x$, $Mo_{12}BiFe_3Co_{4.5}ni_{2.5}Mn_{0.5}K_{0.1}O_x$ and $Mo_{12}BiFe_3Co_{4.5}Ni_{2.5}La_{0.5}K_{0.1}O_x$), U.S. Pat. No. 3,911,039 ($Mo_{12}BiFe_3Co_{4.5}Ni_{2.5}Sn_{0.5}K_{0.1}O_x$), DE-A 25 30 959 and DE-A 24 47 825 ($Mo_{12}BiFe_3Co_{4.5}Ni_{2.5}W_{0.5}K_{0.1}O_x$).

Suitable multimetal oxides and the production thereof are additionally described in U.S. Pat. No. 4,423,281 ($Mo_{12}BiNi_8Pb_{0.5}Cr_3K_{0.2}O_x$ and $Mo_{12}Bi_bNi_7Al_3Cr_{0.5}K_{0.5}O_x$), U.S. Pat. No. 4,336,409 ($MO_{12}BiNi_6Cd_2Cr_3P_{0.5}O_x$), DE-A 26 00 128 ($Mo_{12}BiNi_{0.5}Cr_3P_{0.5}Mg_{7.5}K_{0.1}O_x+SiO_2$) and DE-A 24 40 329 ($Mo_{12}BiCo_{4.5}Ni_{2.5}Cr_3P_{0.5}K_{0.1}O_x$).

Particularly preferred catalytically active multimetal oxides comprising molybdenum and at least one further metal have the general formula (Ia):

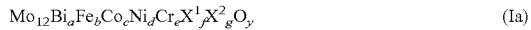

$$Mo_{12}Bi_aFe_bCo_cNi_dCr_eX^1_fX^2_gO_y \qquad (Ia)$$

where
$X^1$=Si, Mn and/or Al,
$X^2$=Li, Na, K, Cs and/or Rb, $0.2 \le a \le 1$, $0.5 \le b \le 10$, $0 \le c \le 10$, $0 \le d \le 10$, $2 \le c+d \le 10$, $0 \le e \le 2$, $0 \le f \le 10$, $0 \le g \le 0.5$, y=a number which, with the prerequisite of charge neutrality, is determined by the valency and prevalence of the elements other than oxygen in (Ia).

Preference is given to catalysts whose catalytically active oxide material comprises, of the two metals Co and Ni, only Co (d=0). $X^1$ is preferably Si and/or Mn and $X^2$ is preferably K, Na and/or Cs, it being particularly preferred when $X^2$=K.

The gas comprising molecular oxygen generally comprises more than 10 vol %, preferably more than 15 vol % and even more preferably more than 20 vol % of molecular oxygen. Said gas is preferably air. The upper limit for the content of molecular oxygen is generally not more than 50 vol %, preferably not more than 30 vol % and even more preferably not more than 25 vol %. The gas comprising molecular oxygen may further comprise any desired inert gases. Examples of possible inert gases include nitrogen, argon, neon, helium, CO, $CO_2$ and water. For nitrogen, the amount of inert gases is generally not more than 90 vol %, preferably not more than 85 vol % and even more preferably not more than 80 vol %. In the case of constituents other than nitrogen, said amount is generally not more than 10 vol %, preferably not more than 1 vol %.

To carry out the oxidative dehydrogenation at full conversion of n-butenes, preference is given to a gas mixture having a molar oxygen:n-butenes ratio of at least 0.5. Preference is given to operating with an oxygen:n-butenes ratio of from 0.55 to 10. This value may be adjusted by mixing the input gas with oxygen or one or more oxygenous gases, for example air, and optionally additional inert gas or steam. The oxygenous gas mixture obtained is then supplied to the oxydehydrogenation.

The reaction temperature of the oxydehydrogenation is generally controlled by a heat-transfer medium surrounding the reaction tubes. Examples of suitable liquid heat-transfer media of this type include melts of salts such as potassium nitrate, potassium nitrite, sodium nitrite and/or sodium nitrate, and melts of metals such as sodium, mercury and alloys of various metals. However, ionic liquids or heat-transfer oils may also be used. The temperature of the heat-transfer medium is between 220° C. to 490° C., preferably between 300° C. to 450° C. and more preferably between 350° C. and 420° C.

A consequence of the exothermicity of the reactions taking place is that, during the reaction, the temperature in certain sections of the reactor interior may be higher than the temperature of the heat-transfer medium thus leading to hotspot formation. The position and magnitude of the hotspot is decided by the reaction conditions, but it can also be regulated through the dilution ratio of the catalyst layer or the flow rate of mixed gas. The temperature difference between a hotspot and the heat transfer medium is generally between 1° C. to 150° C., preferably between 10° C. to 100° C. and more preferably between 20° C. to 80° C. The temperature at the end of the catalyst bed is generally between 0° C. to 100° C., preferably between 0.1° C. to 50° C., more preferably between 1° C. to 25° C. higher than the temperature of the heat transfer medium.

The oxydehydrogenation may be performed in any prior art fixed bed reactor, for example in a staged oven, in a fixed bed tubular reactor or shell and tube reactor, or in a plate heat exchanger reactor. A shell and tube reactor is preferred.

The oxidative dehydrogenation is preferably performed in fixed bed tubular reactors or fixed bed shell and tube reactors. The reaction tubes (similarly to the other elements of the shell and tube reactor) are generally manufactured from steel. The wall thickness of the reaction tubes is typically from 1 to 3 mm. The internal diameter thereof is generally (uniformly) from 10 to 50 mm or from 15 to 40 mm, often from 20 to 30 mm. The number of reaction tubes accommodated in a shell and tube reactor generally totals at least 1000, or 3000, or 5000, preferably at least 10 000. The number of reaction tubes accommodated in the shell and tube reactor is often from 15 000 to 30 000, to 40 000 or to 50 000. The length of the reaction tubes normally extends to just a few meters, a typical reaction tube length being in the range of from 1 to 8 m, often from 2 to 7 m, in many cases from 2.5 to 6 m.

The invention is more particularly elucidated hereinbelow with reference to FIGS. 1 to 4.

The liquid n-butenes-comprising stream a0 is brought into thermal contact with the recycled cooling medium from the quench stage 3 or with part of the recycled cooling medium, for example the aqueous phase, in the heat exchanger 0.

The catalyst bed installed in the ODH reactor 1 may consist of a single layer or of 2 or a sequence of variable layers (called a structured bed). These layers may consist of pure catalyst or may be diluted with a material reactive toward neither the input gas nor components of the product gas from the reaction. Furthermore, the catalyst layers may consist of shaped bodies of all-active material or supported coated catalysts.

The product gas stream 2 exiting the oxidative dehydrogenation comprises not only butadiene but generally also unconverted 1-butene and 2-butene, oxygen and steam. Generally, said stream further comprises as secondary components carbon monoxide, carbon dioxide, inert gases (primarily nitrogen), low-boiling hydrocarbons such as methane, ethane, ethene, propane and propene, butane and isobutane, possibly hydrogen and possibly oxygen-containing hydrocarbons known as oxygenates. Oxygenates may, for example, be formaldehyde, furan, acetaldehyde, acetic acid, maleic anhydride, formic acid, methacrolein, acrolein, propionaldehyde, methacrylic acid, crotonaldehyde, crotonic acid, propionic acid, acrylic acid, methyl vinyl ketone, styrene, benzaldehyde, benzoic acid, phthalic anhydride, fluorenone, anthraquinone and butyraldehyde.

The product gas stream 2 at the reactor outlet is characterized by a temperature close to the temperature at the end of the catalyst bed. The product gas stream is then brought to a temperature of from 150° C. to 400° C., preferably from 160° C. to 300° C., more preferably from 170° C. to 250° C. It is possible to insulate the line through which the product gas stream flows or to employ a heat exchanger in order to keep the temperature within the desired range. This heat exchanger system may be of any desired type provided that said system can be used to keep the temperature of the product gas at the desired level. Examples of a heat exchanger include spiral heat exchangers, plate heat exchangers, double tube heat exchangers, multitube heat exchangers, boiler-spiral heat exchangers, boiler-shell heat exchangers, liquid-liquid contact heat exchangers, air heat exchangers, direct contact heat exchangers and fin tube heat exchangers. Since a portion of the high-boiling by-products present in the product gas may precipitate out during adjustment of the product gas temperature to the desired temperature, the heat exchanger system should thus preferably comprise two or more heat exchangers. When two or more heat exchangers provided are arranged in parallel to enable distributed cooling of the obtained product gas in the heat exchangers, the amount of high-boiling by-products deposited in the heat exchangers decreases and the service life thereof can therefore be extended. As an alternative to the abovementioned method, the two or more heat exchangers provided may be arranged in parallel. The product gas is supplied to one or more, but not to all, heat exchangers, which are relieved by other heat exchangers after a certain operating duration. In this method, cooling can be continued, some of the reaction heat can be recovered and, simultaneously, the high-boiling by-products deposited in one of the heat exchangers can be removed. It is possible to use as an abovementioned organic solvent any solvent provided that it is capable of dissolving the high-boiling by-products. Examples include aromatic hydrocarbon solvents, for example toluene and xylenes, and alkaline aqueous solvents, for example an aqueous solution of sodium hydroxide.

A large proportion of the high-boiling secondary components and of the water is then removed from the product gas stream 2 by chilling and compression. In accordance with the invention the chilling is effected by contacting with a cooling medium which comprises an organic solvent and in one embodiment comprises an aqueous and an organic phase. This stage is also referred to hereinbelow as the quench. This quench may consist of only one stage (3 in FIGS. 1 to 3) or of a plurality of stages (for example 3, 8 in FIGS. 1 to 3). The product gas stream 2 is thus directly contacted with the cooling medium 6 and thereby cooled. The organic phase comprises organic solvents, preferably aromatic hydrocarbons, more preferably toluene, o-xylene, m-xylene, p-xylene, mesitylene, all possible constitutional isomers of mono-, di- and triethylbenzene or mixtures thereof. Preference is also given to aromatic hydrocarbons having a boiling point of more than 120° C. at 1013.25 hPa or mixtures thereof.

Depending on the presence and temperature level of a heat exchanger upstream of the quench 3, the temperature of the product gas 2 is generally from 100° C. to 440° C. The product gas is contacted with the cooling medium in the quench stage 3. When a biphasic cooling medium composed of an aqueous phase and an organic phase is employed, the cooling medium will preferably be introduced via a nozzle in order to achieve the most efficient possible mixing of the aqueous phase and the organic phase on the one hand, and of the biphasic cooling medium with the product gas on the other hand. The same purpose may be served by introducing internals into the quench stage, for example further nozzles, the product gas and the cooling medium passing therethrough together. The coolant inlet into the quench is designed such that blockage by deposits in the region of the coolant inlet is minimized.

The first quench stage 3 generally cools the product gas 2 to from 5° C. to 180° C., preferably to from 30° C. to 130° C. and even more preferably to from 50° C. to 110° C. The temperature of the cooling medium 6 at the inlet may generally be from 5° C. to 200° C., preferably from 20° C. to 120° C., more preferably from 30° C. to 90° C. The pressure in the first quench stage 3 is not subject to particular restriction, but is generally from 0.01 to 5 bar (g), preferably from 0.1 to 2 bar (g) and more preferably from 0.2 to 3 bar (g). The quench stage 3 is generally a cooling tower. The cooling medium 6 employed in the cooling tower is employed in circulating fashion in a quench circuit. Circulation may be ensured via a suitable pump. The temperature of the cooling medium in the quench circuit may optionally be controlled via a heat exchanger. The circulation flow rate of the cooling medium in liters per hour relative to the mass flow rate of butadiene in grams per hour may generally be from 0.0001 to 5 l/g, preferably from 0.001 to 1 l/g and more preferably from 0.002 to 0.2 l/g.

The temperature of the biphasic cooling medium 6 in the bottom may generally be from 15° C. to 210° C., preferably from 25° C. to 130° C., more preferably from 35° C. to 95° C. Depending on the temperature, pressure and water content of the product gas 2, there may additionally be condensation of water in the first quench stage 3. Since the loading of the organic phase and the aqueous phase with secondary components increases over time, some of the cooling medium may be withdrawn from circulation as purge stream 6b and the amount circulating may be kept constant by adding less heavily laden organic phase 5a and less heavily laden aqueous phase 4a. The ratio of volume discharged to volume added depends on the vapor loading of the product gas and the product gas temperature at the end of the first quench stage. The locations for the feeds and draws are not subject to particular restriction. They may, for example, be upstream or downstream of the pump or the heat exchanger.

Figure 2:
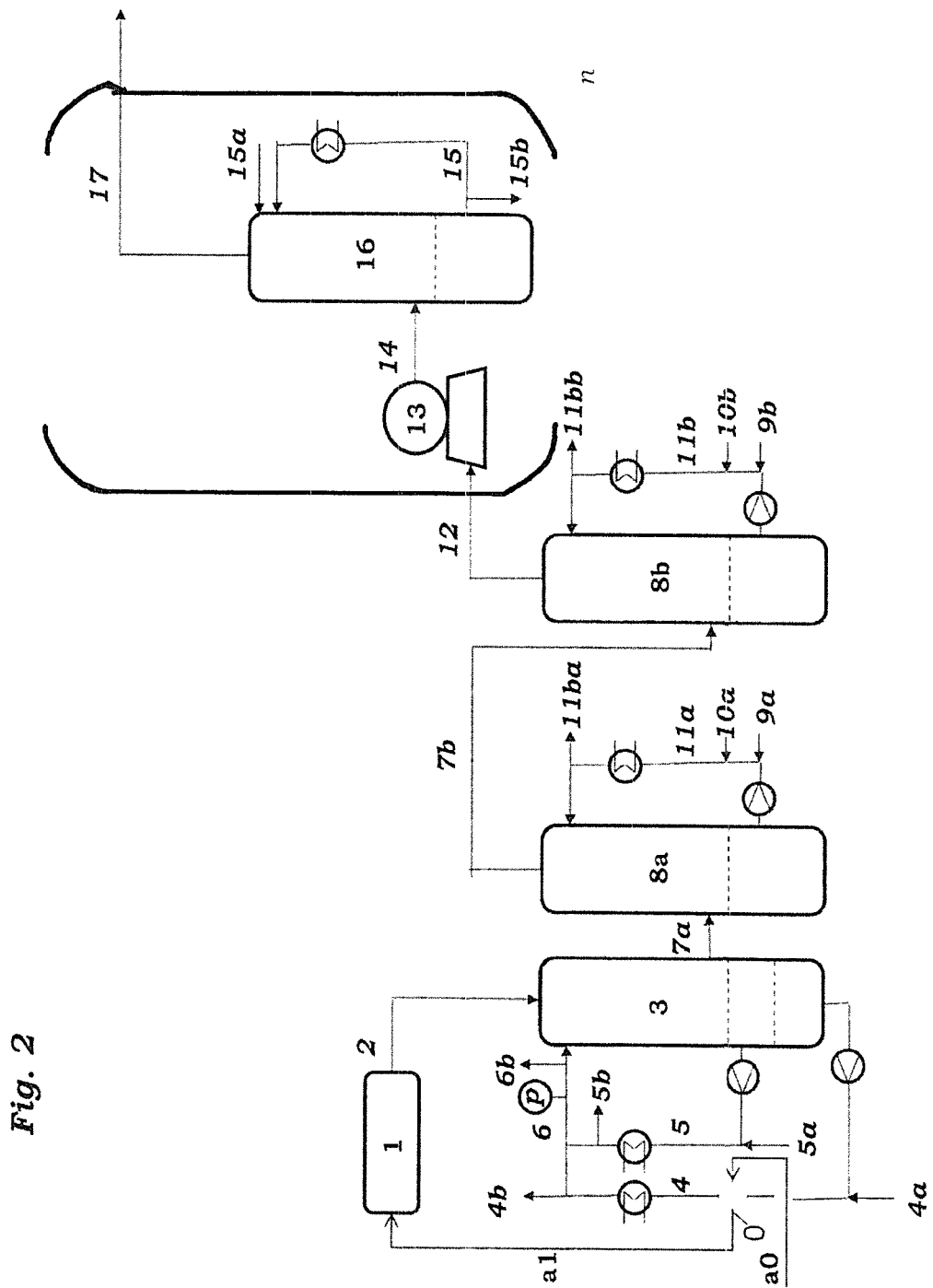
FIG. 2 shows an embodiment in which a predominantly aqueous phase 4 is withdrawn from the bottom of the quench stage 3 and recycled.
Figure 3:
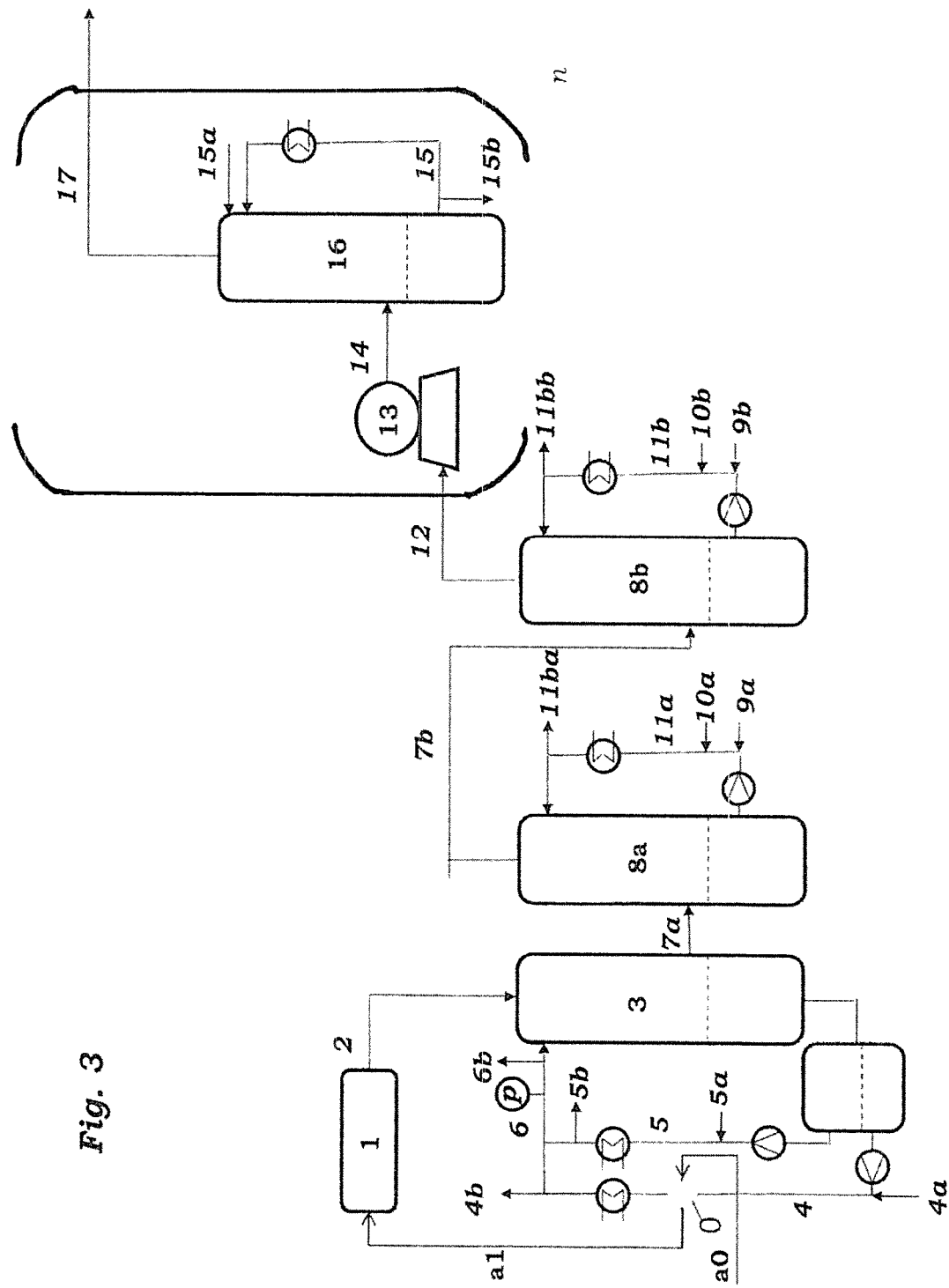
FIG. 3 shows an embodiment in which a predominantly aqueous phase 4 is removed in an additional phase separator.

In the bottom of the quench stage 3, a predominantly aqueous phase 4 may form, which may additionally comprise water-soluble secondary components. As shown in FIG. 2, said phase may be withdrawn from the bottom of the quench stage 3 and recycled. As shown in FIG. 3, the aqueous phase 4 may also be removed in an additional phase separator. Said phase separator may be within the quench circuit for example. The aqueous phase 4 is at least partially recycled into the quench. The organic phase 5 too is at least partially recycled into the quench. A water purge stream 4b and an organic purge stream 5b may also be removed instead of or in addition to the purge stream 6b.

According to FIG. 1, the biphasic cooling medium 6 is brought into thermal contact with the liquid n-butenes-comprising input stream a0 in the heat exchanger 0. According to FIGS. 2 and 3, the removed aqueous phase 4 of the biphasic cooling medium 6 is brought into thermal contact with the liquid n-butenes-comprising input stream a0 in the heat exchanger 0.

In one preferred embodiment, the quench comprises two stages (comprising the stages 3 and 8a according to FIGS. 1 to 3), i.e. stage Ca) and comprises two chilling stages Ca1) and Ca2) in which the product gas stream b is contacted with the chilling medium. In one embodiment at least the cooling medium in the first quench stage is biphasic. The two quench stages may be in separate cooling towers or in a common cooling tower.

The chilled product gas stream 7a possibly depleted of secondary components is supplied to a second quench stage 8a. In this stage, said stream is again contacted with a cooling medium 11a. The cooling medium 11a may be biphasic and may comprise an aqueous phase and an organic phase. However, said medium may also consist predominantly or exclusively of an organic solvent.

The organic solvent preferably comprises aromatic hydrocarbons, more preferably toluene, o-xylene, m-xylene, p-xylene, mesitylene, all possible constitutional isomers of mono-, di- and triethylbenzene and all possible constitutional isomers of mono-, di- and triisopropylbenzene or mixtures thereof. Preference is further given to aromatic hydrocarbons having a boiling point of more than 120° C. at 1013.25 hPa, or mixtures thereof. Said solvent is preferably the same organic solvent as employed in the first quench stage.

The product gas is generally cooled to from 5° C. to 100° C., preferably to from 15° C. to 85° C. and preferably to from 20° C. to 70° C. before it reaches the gas outlet of the second quench stage 8a. The coolant may be supplied in countercurrent to the product gas. In this case, the temperature of the coolant medium 11a at the coolant inlet may be from 5° C. to 100° C., preferably from 15° C. to 85° C., in particular from 30° C. to 70° C. The pressure in the second quench stage 8a is not subject to particular restriction but is generally from 0.01 to 4 bar (g), preferably from 0.1 to 2 bar (g) and more preferably from 0.2 to 1 bar (g). The second quench stage 8a is preferably a cooling tower. The cooling medium 11a used in the cooling tower is employed in circulating fashion in a quench circuit. The circulation flow rate of the cooling medium 11a in liters per hour relative to the mass flow rate of butadiene in grams per hour may generally be from 0.0001 to 5 l/g, preferably from 0.001 to 1 l/g and more preferably from 0.002 to 0.2 l/g.

Since the loading of the cooling medium 11a with secondary components increases over time, some of the cooling medium may be withdrawn from circulation as purge stream 11ba and the amount circulating may be kept constant by adding less heavily laden organic phase 10a and, optionally, less heavily laden aqueous phase 9a.

The temperature of the cooling medium 11a in the bottom may generally be from 20° C. to 210° C., preferably from 35° C. to 120° C., more preferably from 45° C. to 85° C. Depending on the temperature, pressure and water content of the product gas 7a, there may additionally be condensation of water in the second quench stage 8a. In this case, an additional aqueous phase may form in the bottom. The aqueous phase may also be removed in an additional phase separator. Said phase separator may be within the quench circuit for example. The aqueous phase may be withdrawn or at least partially recycled into the quench. The phase separator may alternatively be disposed in the purge stream 11ba for example.

The aqueous phase may be at least partially withdrawn as purge stream or at least partially recycled into the quench. Likewise, the organic phase may be at least partially withdrawn as a purge stream or at least partially recycled into the quench.

The locations for the feeds and draws in the circuits of the respective quench stages are not subject to particular restriction. They may, for example, be upstream or downstream of the pump or the heat exchanger. In addition, the location of the heat exchanger(s) in the quench circuit is not subject to particular restriction. In the case of partially phase-separated quench circuits, heat exchangers may be disposed in one or both circuits, or only in the recombined circuits. It is alternatively possible for heat exchangers to be eschewed altogether and for the quench cooling to be accomplished solely by evaporation of the coolant. In addition, the location of the circulation pumps is not subject to particular restriction. In the case of a phase separator in the circulation stream a pump for example may be present upstream of the phase separator or one pump may be present in each of the phase-separated circuits.

In order to achieve the best possible contact of product gas and cooling medium, the second quench stage 8a may comprise internals. Examples of such internals include bubble-cap, centrifugal and/or sieve trays, columns comprising structured packings, for example sheet metal packings having a specific surface area of from 100 to 1000 $m^2/m^3$ such as Mellapak® 250 Y, and random-packed columns.

The coolant circuits of the quench stages may either be separate from one another or connected to one another. Thus, for instance, some of stream 11ba may be supplied to stream 6 and at least partially replace the streams 4a and/or 5a. The desired temperature of the circulating streams may be established via suitable heat exchangers.

In one preferred embodiment of the invention the chilling stage Ca) is thus performed in two stages, the secondary-components-laden organic solvent from the second stage Ca2) being passed into the first stage Ca1). The organic solvent withdrawn from the second stage Ca2) comprises a reduced amount of secondary components compared to the organic solvent withdrawn from the first stage Ca1).

Stage Ca) may also be performed in a plurality of stages in stages Ca1) to Can), performance in three stages Ca1), Ca2) and Ca3) being particularly preferred. Here, at least some of the cooling medium may be supplied as chillant to the second stage Ca2) after it has passed through the third stage Ca3).

In one particularly preferred embodiment, the quench comprises three stages (comprising stages 3, 8a and 8b according to FIGS. 1 to 3), i.e. stage Ca) comprises three chilling stages Ca1), Ca2) and Ca3) in which the product gas stream b is contacted with the chilling medium. In accordance with the invention at least the cooling medium in the first quench stage is biphasic. The three chilling stages may be in separate cooling towers or in a common cooling tower.

Here, the chilled product gas stream 7a possibly depleted of secondary components is supplied to a second quench stage 8a and the product gas stream 7b possibly further depleted of secondary components is supplied to a third quench stage 8b. Said product gas stream is again contacted with a cooling medium 11b in these quench stages. The cooling medium 11b may be biphasic and may comprise an aqueous phase and an organic phase. However, said medium may also consist predominantly or exclusively of an organic solvent.

It is preferable when the organic solvent in all three quench stages is the same.

The coolant circuits of the three quench stages may either be separate from one another or connected to one another.

In one particularly preferred embodiment of the invention the chilling stage Ca) is thus performed in three stages, the secondary-components-laden organic solvent of the second stage Ca2) being passed into the first stage Ca1) and the less heavily secondary-components-laden organic solvent of the third stage Ca3) being passed into the second stage Ca2).

In a further embodiment in the third chilling stage Ca3) a fresh cooling medium composed of an organic solvent or a mixture of organic solvent and water is introduced into the chilling stage in single pass and in countercurrent, said cooling medium being as yet unladen with the secondary components. Since the fresh cooling medium is as yet unladen with the secondary components to be removed in the quench stages, a further reduction in the secondary components unwanted in the product gas is achieved in the top product of the cooling tower.

To assure the liquid space velocity required for the design of the cooling tower in the chilling stage Ca3), the diameter chosen for this chilling stage Ca3) may be smaller than the diameter of the chilling stages Ca1) and Ca2). When the required liquid space velocity in the chilling stage Ca3) cannot be achieved by reducing the diameter the liquid space velocity in this section is increased accordingly via pumped circulation of the cooling medium.

In one embodiment of the invention the first chilling stage Ca1) is arranged in parallel in duplicate switchable fashion. In normal operation only one of the two parallel chilling stages is operated while the other is out of use for cleaning operations or is available as a reserve.

Entrainment of liquid constituents from the quench into the offgas line may be minimized by taking suitable physical measures, for example installation of a demister. High-boiling substances and other substances not removed from the product gas in the quench may further be removed from the product gas via further physical measures, for example further gas scrubs.

A gas stream 12 is obtained which comprises n-butane, 1-butene, 2-butenes, butadiene, possibly oxygen, hydrogen, steam, small amounts of methane, ethane, ethene, propane and propene, isobutane, carbon oxides, inert gases and fractions of the solvent used in the quench. This gas stream 12 may further comprise remaining traces of high-boiling components not removed quantitatively in the quench.

The gas stream b from chilling step Ca), which stream has been depleted in high-boiling secondary components, is subsequently chilled in step Cb) in at least one compression stage Cba) and preferably in at least one chilling stage Cbb) by contacting with an organic solvent as chillant.

Product gas stream 12 from the coolant quench (3, or preferably 3 and 8a, or preferably 3, 8a and 8b) is compressed in at least one compression stage 13 and subsequently chilled further in the cooling apparatus 16.

The compression and cooling of the gas stream 12 may be effected in one stage or in a plurality of stages (n stages). Overall, the stream is generally compressed from a pressure in the range from 1.0 to 4.0 bar (absolute) to a pressure in the range from 3.5 to 20 bar (absolute). Each compression stage is followed by a chilling stage in which the gas stream is chilled to a temperature in the range from 15° C. to 60° C. Cooling may be effected by direct or indirect heat transfer.

To cool stream 14 directly and/or to remove further secondary components from stream 14, stream 14 is contacted with a coolant 15. The cooling medium 15 may be monophasic or biphasic and may comprise an aqueous phase and an organic phase. In one preferred embodiment the organic phase comprises the same organic solvent as the quench coolants 6, 11a and 11b. The cooling results in condensation of water and of organic solvent used in the quench and possibly of further secondary components. Since the loading of the coolant 15 with secondary components increases over time, some of the laden coolant may be drawn off from the circuit as stream 15b and the amount of the coolant circulating may be kept constant by adding less heavily laden coolant 15a.

The coolant 15 may be chilled in a heat exchanger and recycled into the apparatus 16 as coolant.

The condensate stream 15b may be fed into stream 5a and/or 10a and/or 10b and hence recycled into the circulation stream 6 and/or 11a and/or 11b of the quench. This allows the $C_4$ components absorbed in the condensate stream 15a to be brought back into the gas stream thus increasing the yield.

What remains is a gas stream 17 comprising butadiene, 1-butene, 2-butenes, oxygen, steam, possibly low-boiling hydrocarbons such as methane, ethane, ethene, propane and propene, butane and isobutane, possibly carbon oxides and possibly inert gases. This product gas stream may further comprise traces of high-boiling components.

Examples of suitable compressors include turbo compressors, rotary piston compressors and reciprocating piston compressors. The compressors may be driven with an electric motor, an expander or a gas or steam turbine for example. Typical compression ratios (exit pressure:entry pressure) per compressor stage are between 1.5 and 3.0 depending on type. The chilling of the compressed gas is effected with organic solvent-purged heat exchangers or organic quench stages, which may be shell and tube, spiral or plate heat exchangers for example. Employed in these heat exchangers as coolant are cooling water or heat transfer oils. Preference is additionally given to the use of air cooling using blowers.

The gas stream 17 comprising butadiene, n-butenes, oxygen, low-boiling hydrocarbons (methane, ethane, ethene, propane, propene, n-butane, isobutane), possibly steam, possibly carbon oxides and possibly inert gases and possibly traces of secondary components is sent, as a starting stream, for further processing.

Figure 4:
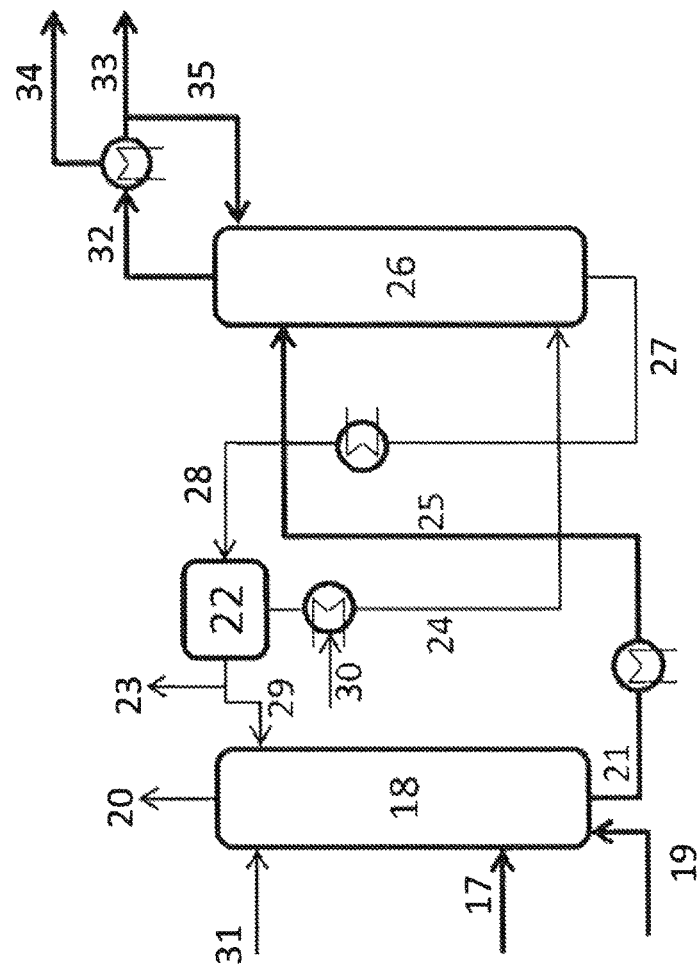
FIG. 4 shows an embodiment in which step D) comprises steps Da) to Dc).

A step D) shown in FIG. 4 comprises removing noncondensable and low-boiling gas constituents comprising oxygen, low-boiling hydrocarbons (methane, ethane, ethene, propane, propene), carbon oxides and inert gases from the process gas stream 17 in an absorption column as a gas stream by absorbing the $C_4$ hydrocarbons in a high-boiling absorption medium (29 and/or 31) and subsequently desorbing the $C_4$ hydrocarbons. It is preferable when step D), as shown in FIG. 4, comprises the steps Da) to Dc):

Da) absorbing the $C_4$ hydrocarbons comprising butadiene and n-butenes into a high-boiling absorption medium (29 and/or 31) to obtain a $C_4$-hydrocarbons-laden absorption medium stream and gas stream 20, Db) removing oxygen from the $C_4$-hydrocarbons-laden absorption medium stream from step Da) by stripping with a noncondensable gas stream 19 to obtain a $C_4$-hydrocarbons-laden absorption medium stream 21 and Dc) desorbing the $C_4$ hydrocarbons from the laden absorption medium stream to obtain a $C_4$ product gas stream 32 which consists essentially of $C_4$ hydrocarbons.

To this end in absorption stage 18 the gas stream 17 is contacted with an inert absorption medium and the $C_4$ hydrocarbons are absorbed into the inert absorption medium to obtain a $C_4$-hydrocarbons-laden absorption medium and an offgas 20 comprising the remaining gas constituents. The $C_4$ hydrocarbons are liberated from the high-boiling absorption medium again in a desorption stage.

The absorption stage may be performed in any desired suitable absorption column known to those skilled in the art. The absorption may be effected by simply passing the product gas stream through the absorption medium. However, said absorption may also be effected in columns or in rotary absorbers. Said absorption may be operated in cocurrent, countercurrent or crosscurrent. The absorption is preferably performed in countercurrent. Examples of suitable absorption columns include tray columns comprising bubble-cap, centrifugal and/or sieve trays, columns comprising structured packings, for example sheet metal packings having a specific surface area of 100 to 1000 $m^2/m^3$ such as Mellapak® 250 Y, and random-packed columns. Also suitable, however, are trickle towers and spray towers, graphite block absorbers, surface absorbers such as thick-film and thin-film absorbers, and also rotary columns, plate scrubbers, cross-spray scrubbers and rotary scrubbers.

In one embodiment the gas stream 17 comprising butadiene, n-butenes and the low-boiling and noncondensable gas constituents is supplied to the lower region of an absorption column. The high-boiling absorption medium (29 and/or 31) is introduced in the upper region of the absorption column.

Inert absorption media used in the absorption stage are generally high-boiling nonpolar solvents in which the $C_4$ hydrocarbon mixture to be removed has a markedly higher solubility than do the remaining gas constituents to be removed. Suitable absorption media are comparatively nonpolar organic solvents, for example aliphatic $C_8$ to $C_{18}$ alkanes, or aromatic hydrocarbons such as the middle oil fractions from paraffin distillation, toluene or ethers comprising bulky groups, or mixtures of these solvents, where these may comprise an added polar solvent such as 1,2-dimethylphthalate. Further suitable absorption media are esters of benzoic acid and phthalic acid with straight-chain $C_1$-$C_8$alkanols, and so-called heat transfer oils, such as biphenyl and diphenyl ethers, chlorine derivatives thereof and triarylalkenes. One suitable absorption medium is a mixture of biphenyl and diphenyl ether, preferably in the azeotropic composition, for example the commercially available product Diphyl®. This solvent mixture often comprises dimethyl phthalate in an amount of from 0.1 to 25 wt %.

In one preferred embodiment the absorption stage Da) employs the same solvent as the chilling stage Ca).

Preferred absorption media are solvents having a dissolution capacity for organic peroxides of at least 1000 ppm (mg of active oxygen/kg of solvent). The preferred embodiment employs toluene, o-xylene, m-xylene, p-xylene, mesitylene or mixtures thereof as solvent for the absorption.

Withdrawn at the top of the absorption column 18 is an offgas stream 20 essentially comprising oxygen, low-boiling hydrocarbons (methane, ethane, ethene, propane, propene), possibly $C_4$ hydrocarbons (butane, butenes, butadiene), possibly inert gases, possibly carbon oxides and possibly also water vapor. Some of this stream may be supplied to the ODH reactor. This makes it possible, for example, to set the feed stream of the ODH reactor to the desired $C_4$ hydrocarbon content.

At the bottom of the absorption column in a further column residues of oxygen dissolved in the absorption medium are discharged by purging with a gas 19. The fraction of oxygen remaining is to be sufficiently small that the stream 32 which comprises butane, butene and butadiene and leaves the desorption column comprises only no more than 100 ppm of oxygen.

The stripping-out of the oxygen in step Db) may be performed in any desired suitable column known to those skilled in the art. The stripping may be effected simply by passing noncondensable gases, preferably inert gases such as nitrogen, through the laden absorption solution. $C_4$ hydrocarbons stripped out at the same time are scrubbed back into the absorption solution in the upper portion of the absorption column 18 by passing the gas stream back into this absorption column. This may be effected either via connection of the stripper column by pipework or via direct mounting of the stripper column below the absorber column. This direct coupling may be effected since in accordance with the invention the pressure in the stripping column section and in the absorption column section is the same. Examples of suitable stripping columns include tray columns comprising bubble-cap, centrifugal and/or sieve trays, columns comprising structured packings, for example sheet metal packings having a specific surface area of 100 to 1000 $m^2/m^3$ such as Mellapak® 250 Y, and random-packed columns. Also suitable, however, are trickle towers and spray towers, and also rotary columns, plate scrubbers, cross-spray scrubbers and rotary scrubbers. Examples of suitable gases include nitrogen and methane.

The absorbent stream 21 laden with $C_4$ hydrocarbons may be heated up in a heat exchanger and then passed as stream 25 into a desorption column 26. In one version of the process, the desorption step Dc) is performed by decompressing and/or heating the laden absorption medium. A preferred version of the process is the utilization of a vapor stream 24 which is supplied in the bottom of the desorption column 26.

The absorption medium regenerated in the desorption stage is withdrawn from the desorption column 26 as stream 27 together with the condensed water. This biphasic mixture may be chilled in a heat exchanger and separated in a decanter 22 as stream 28 into an aqueous stream and an absorbent stream 29. The absorbent stream 29 will be returned to the absorber column 18 while the aqueous stream is evaporated in an evaporator to generate stream 24. In addition or as an alternative, additional water (stream 30) may also be evaporated in the evaporator.

Low boilers present in the process gas stream, for example ethane or propane, and high-boiling components, such as benzaldehyde, maleic anhydride and phthalic anhydride, may accumulate in the circulation stream. A purge stream 23 may be drawn off to limit accumulation.

The $C_4$ product gas stream 32 consisting essentially of n-butane, n-butenes and butadiene generally comprises from 20 to 80 vol % of butadiene, from 0 to 80 vol % of n-butane, from 0 to 10 vol % of 1-butene and from 0 to 50 vol % of 2-butenes, the total amount summing to 100 vol %. Said stream may further comprise small amounts of isobutane.

Some of the condensed, primarily $C_4$-hydrocarbons-comprising top output from the desorption column is recycled into the top of the column as stream 35 to enhance the separation performance of the column.

The liquid (stream 33) or gaseous (stream 34) $C_4$ product streams exiting the condenser are subsequently separated in step E) by extractive distillation with a butadiene-selective solvent to afford a stream comprising butadiene and the selective solvent and a stream comprising n-butenes.

The extractive distillation may be performed, for example, as described in "Erdöl and Kohle-Erdgas-Petrochemie", volume 34 (8), pages 343 to 346, or "Ullmanns Enzyklopädie der Technischen Chemie", volume 9, 4th edition 1975, pages 1 to 18. This comprises contacting the $C_4$ product gas stream with an extractant, preferably an N-methylpyrrolidone (NMP)/water mixture, in an extraction zone. The extraction zone is generally in the form of a scrubbing column comprising trays, random packings or structured packings as internals. Said column generally comprises from 30 to 70 theoretical plates in order that sufficient separating action is achieved. The scrubbing column preferably comprises a backwash zone in the top of the column. This backwash zone serves to recover the extractant present in the gas phase with the aid of a liquid hydrocarbon reflux, for which purpose the top fraction is condensed beforehand. The mass ratio of extractant to $C_4$ product gas stream in the feed to the extraction zone is generally from 10:1 to 20:1. The extractive distillation is preferably operated at a bottoms temperature in the range of from 100° C. to 250° C., more particularly at a temperature in the range of from 110° C. to 210° C., an overhead temperature in the range of from 10° C. to 100° C., more particularly in the range of from 20° C. to 70° C. and a pressure in the range of from 1 to 15 bar, more particularly in the range of from 3 to 8 bar. The extractive distillation column preferably comprises from 5 to 70 theoretical plates.

Suitable extractants are butyrolactone, nitriles such as acetonitrile, propionitrile, methoxypropionitrile, ketones such as acetone, furfural, N-alkyl-substituted lower aliphatic acid amides such as dimethylformamide, diethylformamide, dimethylacetamide, diethylacetamide, N-formylmorpholine, N-alkyl-substituted cyclic acid amides (lactams) such as N-alkylpyrrolidones, especially N-methylpyrrolidone (NMP). Alkyl-substituted lower aliphatic acid amides or N-alkyl-substituted cyclic acid amides are generally used. Particularly advantageous are dimethylformamide, acetonitrile, furfural and, in particular, NMP.

However, it is also possible to use mixtures of these extractants with one another, for example of NMP and acetonitrile, mixtures of these extractants with co-solvents and/or tert-butyl ethers, for example methyl tert-butyl ether, ethyl tert-butyl ether, propyl tert-butyl ether, n- or isobutyl tert-butyl ether. NMP is particularly suitable, preferably in aqueous solution, preferably comprising from 0 to 20 wt % of water, more preferably comprising from 7 to 10 wt % of water, more particularly comprising 8.3 wt % of water.

The top product stream from the extractive distillation column comprises essentially butane and butenes and small amounts of butadiene and is drawn off in gaseous or liquid form. The stream consisting essentially of n-butane and 2-butene generally comprises up to 100 vol % of n-butane, from 0 to 50 vol % of 2-butene, and from 0 to 3 vol % of further constituents such as isobutane, isobutene, propane, propene and $C_5^+$ hydrocarbons.

Some or all of the stream consisting essentially of n-butane and 2-butene may be supplied to the $C_4$ feed of the ODH reactor. Since the butene isomers in this recycle stream consist essentially of 2-butenes, and 2-butenes are generally oxidatively dehydrogenated more slowly to butadiene than 1-butene, this recycle stream can be catalytically isomerized before being fed into the ODH reactor. This makes it possible to adjust the isomer distribution according to the isomer distribution present at thermodynamic equilibrium.

A step F) comprises distillatively separating the stream comprising butadiene and the selective solvent into a stream consisting essentially of the selective solvent and a stream comprising butadiene.

The stream obtained at the bottom of the extractive distillation column generally comprises the extractant, water, butadiene and small fractions of butenes and butane and is supplied to a distillation column. Butadiene may be obtained therein overhead or as a side draw. Obtained at the bottom of the distillation column is a stream comprising extractant and possibly water, the composition of the stream comprising extractant and water corresponding to the composition as added to the extraction. The stream comprising extractant and water is preferably returned to the extractive distillation.

When the butadiene is obtained via a side draw the extraction solution thus drawn off is transferred into a desorption zone while the butadiene is once again desorbed and backwashed out of the extraction solution. The desorption zone may, for example, be in the form of a scrubbing column comprising from 2 to 30, preferably from 5 to 20, theoretical plates and optionally a backwash zone comprising, for example, 4 theoretical plates. This backwash zone serves to recover the extractant present in the gas phase with the aid of a liquid hydrocarbon reflux, for which purpose the top fraction is condensed beforehand. Structured packings, trays or random packings are provided as internals. The distillation is preferably performed at a bottoms temperature in the range of from 100° C. to 300° C., more particularly in the range of from 150° C. to 200° C., and an overhead temperature in the range of from 0° C. to 70° C., more particularly in the range of from 10° C. to 50° C. The pressure in the distillation column is preferably in the range of from 1 to 10 bar. The desorption zone is generally operated at reduced pressure and/or elevated temperature relative to the extraction zone.

The desired product stream obtained at the column top generally comprises from 90 to 100 vol % of butadiene, from 0 to 10 vol % of 2-butene and from 0 to 10 vol % of n-butane and isobutane. Further purification of the butadiene may be accomplished by performing a further prior art distillation.

The invention is more particularly elucidated by the example which follows.

EXAMPLE

In a commercial plant for generating 130 000 t/a of butadiene by oxidative dehydrogenation of n-butenes a butene stream of about 27 t/h at a temperature of about 36° C. is to be heated up at a process pressure of about 7 bar and evaporated at an evaporation temperature of about 60° C. The butene stream is heated up and partially evaporated using a substream of about 450 t/h of the organic coolant mesitylene used for chilling the product gas stream from the oxydehydrogenation and taken from the chilling zone Ca). This coolant has a temperature of 66° C. and is chilled to 62° C. in a butane evaporator which is in the form of a straight-tube exchanger with a floating head and vapor separation space (TEMA BES type). The floating-head design makes it possible to clean both the tube side and the shell side as required by pulling the bundle and demounting the floating head. The energy turnover (heat flow) in the evaporator is about 1 MW which corresponds to a saving of about 1.7 t/h of low-pressure steam.

The remaining evaporation of the butene stream is effected in a further heat exchanger heated with low-pressure steam. The heat output of this apparatus is about 1.9 MW which corresponds to a heating steam amount of about 3.3 t/h. This heat exchanger may be a straight-tube heat exchanger with a hairpin sheet and vapor separation space (TEMA BKU type) since experience teaches that the option of cleaning on the steam side is not necessary.

The invention claimed is:

1. A process for producing butadiene from n-butenes, comprising the steps of:
   A) providing a vaporous n-butenes-comprising input gas stream a1 by evaporating a liquid n-butenes-comprising stream a0;
   B) introducing the vaporous n-butenes-comprising input gas stream a1 and an oxygenous gas into at least one oxidative dehydrogenation zone and oxidatively dehydrogenating n-butenes to butadiene to obtain a product gas stream b comprising butadiene, unconverted n-butenes, steam, oxygen, low-boiling hydrocarbons, high-boiling secondary components, possibly carbon oxides and possibly inert gases;
   Ca) chilling the product gas stream b by contacting with a cooling medium comprising an organic solvent selected from the group consisting of toluene, o-, m- and p-xylene, mesitylene, mono-, di- and triethylbenzene, mono-, di- and triisopropylbenzene and mixtures thereof, wherein the cooling medium comprises an aqueous phase and an organic phase, in at least one chilling zone, the cooling medium being at least partially recycled into the chilling zone,
   Cb) compressing the chilled product gas stream b which is possibly depleted of high-boiling secondary components in at least one compression stage to obtain at least one aqueous condensate stream c1 and a gas stream c2 comprising butadiene, n-butenes, steam, oxygen, low-boiling hydrocarbons, possibly carbon oxides and possibly inert gases,
   D) removing noncondensable and low-boiling gas constituents comprising oxygen, low-boiling hydrocarbons, possibly carbon oxides and possibly inert gases as gas stream d2 from the gas stream c2 by absorbing the $C_4$ hydrocarbons comprising butadiene and n-butenes into an absorption medium to obtain a $C_4$-hydrocarbons-laden absorption medium stream and the gas stream d2 and subsequently desorbing the $C_4$ hydrocarbons from the laden absorption medium stream to obtain a $C_4$ product gas stream d1, wherein at least some of the recycled cooling medium from step Ca) is brought into thermal contact with the liquid n-butenes-comprising stream a0 in one or more indirect heat exchangers and at least some of the liquid n-butenes-comprising stream a0 is evaporated by indirect heat transfer with the recycled cooling medium, and wherein stage Ca) is performed in three stages Ca1), Ca2) and Ca3) in three chilling zones and an organic solvent from the second stage Ca2) which solvent is laden with high-boiling secondary components is passed into the first stage Ca1) and an organic solvent from the third stage Ca3) which solvent is less heavily laden with high-boiling secondary components is passed into the second stage Ca2).

2. The process according to claim 1, wherein at least some of the organic phase is removed and brought into thermal contact with the liquid n-butenes-comprising stream a0.

3. The process according to claim 1, wherein at least some of the aqueous phase is removed and brought into thermal contact with the liquid n-butenes-comprising stream a0.

4. The process according to claim 1, wherein a fresh cooling medium as yet unladen with the high-boiling secondary components is introduced into the third chilling stage Ca3) into the chilling stage in single pass and in counter-current.

5. The process according to claim 1, wherein the indirect heat exchanger(s) in which at least some of the recycled cooling medium is brought into thermal contact with the liquid n-butenes-comprising stream a0 are straight-tube heat exchangers.

6. The process according to claim 1, wherein the temperature of the recycled cooling medium during heat transfer is in the range of from 60° C. to 80° C.

7. The process according to claim 1, wherein the evaporation temperature of the liquid n-butenes-comprising stream a0 is in the range of from 30° C. to 70° C.

8. The process according to claim 1, wherein stage Cb) comprises at least one compression stage Cba) and at least one chilling stage Cbb).

9. The process according to claim 8, wherein the chillant of the chilling stage Cbb) comprises the same organic solvent used in stage Ca) as the organic phase of the cooling medium.

10. The process according to claim 1, wherein stage Cb) comprises a plurality of compression stages Cba1) to Cban) and chilling stages Cbb1) to Cbbn).

11. The process according to claim 1, wherein step D) comprises steps Da) to Dc):
   Da) absorbing the $C_4$ hydrocarbons comprising butadiene and n-butenes into a high-boiling absorption medium to obtain a $C_4$-hydrocarbons-laden absorption medium stream and the gas stream d2,
   Db) removing oxygen from the $C_4$-hydrocarbons-laden absorption medium stream from step Da) by stripping with a noncondensable gas stream, and
   Dc) desorbing the $C_4$ hydrocarbons from the laden absorption medium stream to obtain a $C_4$ product gas stream d1 comprising less than 100 ppm of oxygen.

12. The process according to claim 11, wherein the high-boiling absorption medium employed in step Da) is an aromatic hydrocarbon solvent.

13. The process according to claim 1, wherein step D) is followed by steps E) and F):
   E) separating the $C_4$ product stream d1 into a stream e1 comprising butadiene and the selective solvent and a stream e2 comprising n-butenes by extractive distillation with a butadiene-selective solvent,
   F) distilling the stream e1 comprising butadiene and the selective solvent to obtain a stream f1 consisting essentially of the selective solvent and a stream f2 comprising butadiene.

* * * * *